United States Patent [19]

Geffken et al.

[11] Patent Number: 4,957,933

[45] Date of Patent: Sep. 18, 1990

[54] FUNGICIDAL OXAZOLIDINONES

[75] Inventors: Detlef Geffken, Hamburg, Fed. Rep. of Germany; Rayner Dennis R., Centerville, Del.

[73] Assignee: E. I. du Pont de Nemours and Company, Wilmington, Del.

[21] Appl. No.: 341,741

[22] Filed: Apr. 21, 1989

[51] Int. Cl.$^5$ .............................................. A01N 43/76
[52] U.S. Cl. .................................................... 514/376
[58] Field of Search ......................................... 514/376

[56] References Cited

PUBLICATIONS

Chemical Abstract, vol. 100(1), p. 6469q, 1984.

*Primary Examiner*—Douglas W. Robinson
*Assistant Examiner*—Kevin E. Weddington
*Attorney, Agent, or Firm*—Samuel S. Blight

[57] ABSTRACT

A method of controlling plant disease using thioxooxazolidinones, oxazolidinediones and related heterocycles, and agriculturally suitable compositions containing them.

8 Claims, No Drawings

FUNGICIDAL OXAZOLIDINONES

BACKGROUND OF THE INVENTION

This invention pertains to a novel method-of-use of compounds of Structure I as fungicides for protecting plants from disease.

Processes for the preparation of the compounds described in this invention are disclosed in the following references:
Geffken, D.; *Z. Naturforsch*, 1983, 38b, 1008
Geffken, D.; Zinner, G.; *Chem. Ber.*, 1973, 106, 2246
Geffken, D.; *Arch. Pharm.*, 1982, 315. 802;
Geffken, D. *Z. Naturforsch*, 1987, 42b, 1202
Hanefield, W.; Jalili, M. A., *Arch. Pharm.*, 1987, 320, 367

No particular utility for the compounds is described in the above references.

A new process for the preparation of these compounds is also disclosed in this application, and disclosed and claimed in copending application No. BA-8800.

Compounds related to I are broadly disclosed as medicines, agrochemicals and microbicides in Japanese Patent No. 61/200978-A, and as general biocides in EP No. 249328-A. However, these applications do not encompass compounds of the instant invention, nor do they suggest the use of the compounds of this invention as fungicides particularly effective for the protection of crops against disease.

SUMMARY OF THE INVENTION

This invention comprises the method of use of compounds of Formula I and their agriculturally suitable compositions as broad-spectrum crop protection chemicals,

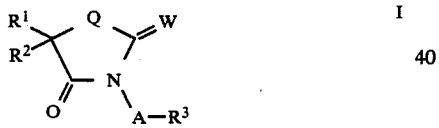

wherein;
A is O or $NR^4$,
Q is O or S,
W is O or S,
$R^1$ is H, $C_1$ to $C_6$ alkyl, $C_1$ to $C_6$ haloalkyl, $C_3$ to $C_6$ cycloalkyl, $C_2$ to $C_6$ alkenyl, $C_2$ to $C_6$ alkynyl, $C_2$ to $C_6$ alkoxyalkyl, $C_1$ to $C_3$ phenyl or benzyl, wherein said phenyl or benzyl ring is substituted on the ring with R6, and the benzylic carbon is substituted with R7;
$R^2$ is phenyl substituted with $R^5$ and $R^6$, naphthyl substituted with, 1 to 2 groups selected from $R^6$, thienyl substituted with $R^5$ and $R^6$, furyl substituted with $R^6$, pyridyl substituted with one of the following:
$R^6$, phenoxy substituted with $R^6$, or phenylthio substituted with $R^6$;
$C_1$ to $C_2$ alkyl substituted with phenoxy or phenylthio, said phenoxy or phenylthio being substituted on the ring with $R^6$,
$C_1$ to $C_6$ alkyl; or
$R^1$ and $R^2$ can be taken together, along with the carbon to which they are attached, to form a carbocyclic or heterocyclic ring (containing O, N—$R^7$, or S) of 5 to 7 ring atoms. The heterocyclic ring can be fused with an $R^5$-substituted benzene ring or an $R^6$-substituted thiophene ring, the heteroatom not being attached to the spiro center, the carbocyclic ring can be fused with 1 or 2 $R^5$-substituted benzene rings or with an $R^6$-substituted thiophene ring;
$R^3$ is phenyl substituted with $R^5$ and $R^6$, benzyl substituted on the benzylic carbon with a group selected from $R^7$ and substituted on the phenyl ring with $R^6$, naphthyl substituted with $R^6$, thienyl substituted with $R^6$, furyl substituted with $R^6$, pyridyl substituted with $R^6$, pyrazyl
substituted with $R^6$, pyrimidyl
substituted with $R^6$, pyridazyl
substituted with $R^6$, $C_2$ to $C_{10}$ alkyl, $C_5$ to $C_7$ cycloalkyl;
$R^4$ is hydrogen, formyl, $C_2$ to $C_4$ alkylcarbonyl, $C_2$ to $C_4$ haloalkylcarbonyl, $C_2$ to $C_4$ alkoxyalkylcarbonyl, $C_2$ to $C_4$ alkoxy carbonyl, $C_2$ to $C_5$ alkylaminocarbonyl, $C_1$ to $C_4$ alkylsulfonyl, $C_1$ to $C_6$ alkyl, $C_4$ to $C_6$ cycloalkyl, benzyl substituted with $R^6$ on the phenyl ring and substituted with $R^7$ on the benzylic carbon, phenylaminocarbonyl where said phenyl is substituted with $R^6$, $C_3$ to $C_4$ alkenyl, $C_3$ to $C_4$ alkynyl; or
$R^3$ and $R^4$ can be taken together, along with the nitrogen atom to which they are attached, to form a pyrrolidino, piperidino or hexamethylenimino ring, which rings can be fused to an $R^6$-substituted benzene ring; $R^5$ is hydrogen, halogen, $C_1$ to $C_6$ alkyl, $C_1$ to $C_6$ haloalkyl, $C_1$ to $C_6$ alkoxy, $C_3$ to $C_4$ alkenyloxy, $C_1$ to $C_5$ alkylthio, $C_1$ to $C_4$ haloalkylthio, $C_1$ to $C_4$ haloalkoxy, $C_1$ to $C_4$ alkylsulfonyl, $C_1$ to $C_4$ haloalkylsulfonyl, nitro, phenyl substituted with $R^6$, phenoxy substituted with $R^6$, phenylthio substituted with $R^6$, cyano, $C_3$ to $C_4$ alkynyloxy, $C_2$ to $C_6$ alkoxyalkyl, $C_2$ to $C_6$ alkoxyalkyloxy, phenoxymethyl substituted On the phenyl ring with $R^6$, benzyloxy substituted on the phenyl ring with $R^6$, phenethyloxy substituted on the phenyl ring with $R^6$, phenethyl substituted on the phenyl ring with $R^6$ or benzyl substituted on the phenyl ring with $R^6$, phenoxy substituted with $R^6$, $C_2$ to $C_6$ carboalkoxy, $C_5$ to $C_6$ cycloalkyl;
$R^6$ is hydrogen, 1 to 2 halogen, methyl, trifluoromethyl, $C_1$ to $C_4$ alkoxy, methylthio, nitro;
$R^7$ is hydrogen, $C_1$ to $C_4$ alkyl; provided that, (1) when A is oxygen, $R^3$ is phenyl substituted with $R^5$ and $R^6$,
and (2) when $R^1$ is H, Q is not sulfur.

Preferred for reasons of their greater fungicidal activity and/or more favorable ease of synthesis are:
(1) Compounds of Formula I where A is $NR^4$
(2) Compounds of Preferred 1 where W is sulfur.
(3) Compounds of Preferred 2 where Q is oxygen.
(4) Compounds of Preferred 3 where:
$R^1$ is $C_1$ to $C_4$ alkyl, $C_1$ to $C_4$ haloalkyl, $C_3$ to $C_4$ cycloalkyl, $C_2$ to $C_4$ alkenyl, $C_2$ to $C_4$ alkynyl, $C_2$ to $C_4$ alkoxyalkyl;
$R^2$ is phenyl substituted with $R^5$ and $R^6$, substituted with $R^6$, thienyl substituted with $R^5$ and $R^6$, furyl substituted with $R^6$, pyridyl substituted with $R^6$; or
$R^1$ and $R^2$ can be taken together, along with the carbon to which they are attached, to form a carbocyclic ring of 5 to 6 ring atoms. The carbocyclic ring can be fused with an $R^5$-substituted benzene ring or with an $R^6$-substituted thiophene ring; and $R^3$ is phenyl substituted with $R^5$ and $R^6$, thienyl substituted with $R^6$, furyl substituted with $R^6$, pyridyl substituted with $R^6$.

(5) Compounds of Preferred 4 where:
- $R^1$ is $C_1$ to $C_4$ alkyl, trifluoromethyl, $C_2$ to $C_3$ alkenyl, $C_2$ to $C_3$ alkynyl;
- $R^2$ is phenyl substituted with $R^5$ and $R^6$, thienyl substituted with $R^5$ and $R^6$;
- $R^3$ is phenyl substituted with $R^5$ and $R^6$;
- $R^4$ is hydrogen, $C_1$ to $C_4$ alkyl;
- $R^5$ is hydrogen, halogen, $C_1$ to $C_4$ alkyl, $C_1$ to $C_4$ haloalkyl, $C_1$ to $C_4$ alkoxy, $C_1$ to $C_4$ alkylthio, $C_1$ to $C_4$ alkylsulfonyl, nitro, phenyl substituted with $R^6$, phenoxy substituted with $R^6$;
- $R^6$ is hydrogen, 1 to 2 halogen, methyl, trifluoromethyl, methoxy; and
- $R^7$ is hydrogen.

(6) Compounds of Preferred 5 where:
- $R^5$ is hydrogen, halogen, methyl, trifluoromethyl, methoxy, phenoxy substituted with hydrogen or 1 to 2 of the following: halogen, methyl, methoxy or trifluoromethyl, nitro;
- $R^6$ is hydrogen, halogen, methyl, methoxy, or trifluoromethyl.

Specifically preferred for greatest fungicidal activity and/or ease of synthesis are:

(1)

5-methyl-5-phenyl-3-(phenylamino)-2-thioxo-4-oxazolidinone;

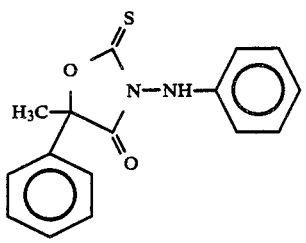

(2)

5-(4-fluorophenyl)-5-methyl-3-(phenylamino)-2-thioxo-4-oxazolidinone;

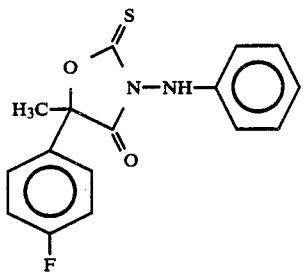

(3)

5-methyl-5-(4-phenoxyphenyl)-3-(phenylamino)-2-thioxo-4-oxazolidinone.

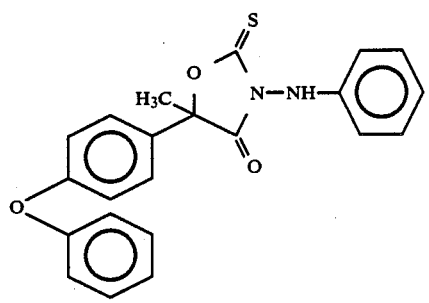

DETAILED DESCRIPTION OF THE INVENTION

Synthesis

The compounds of this invention may be prepared by the route outlined below to 5-methyl-5-phenyl-3-(phenylamino)-2-thioxo-4-oxazolidinone:

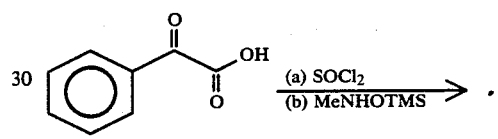

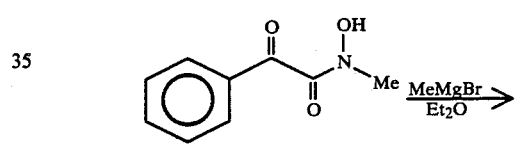

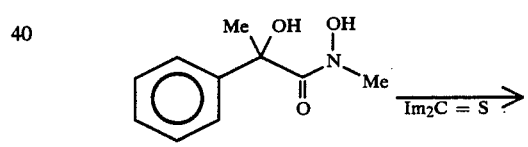

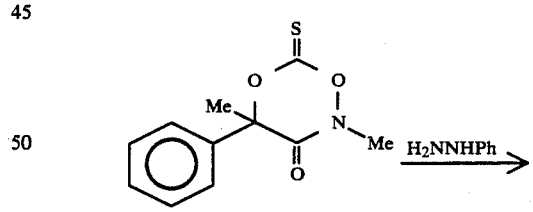

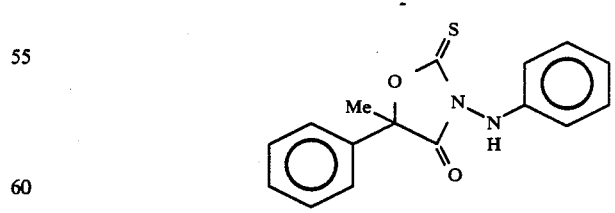

Additionally, a patent application, BA-8800, describing a novel, expeditious synthesis of these compounds is copending.

The compounds of Formula I can be prepared according to one or more of the methods described in Equations 1, 2, 9, 10, 11 and 14.

As shown in Equation 1, compounds of Formula I can be prepared by treating heterocycles of type II with an appropriate amine III.

Equation 1

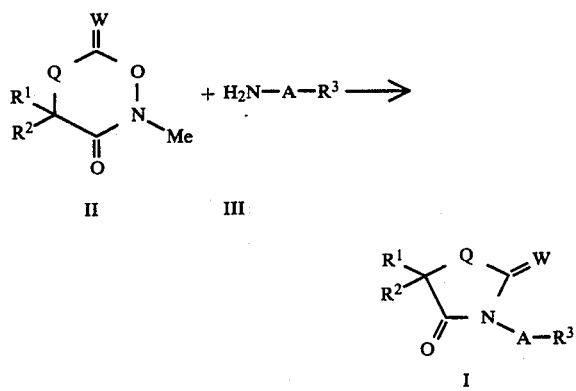

The reactions are conducted at 0° C. to 50° C. in an inert solvent such as methylene chloride, THF, or benzene. Detailed experimental procedures are disclosed in the references cited below.

Compounds described by Formula I wherein Q is O and W is S can be prepared by two methods. The first method is illustrated in Equation 2.

Equation 2

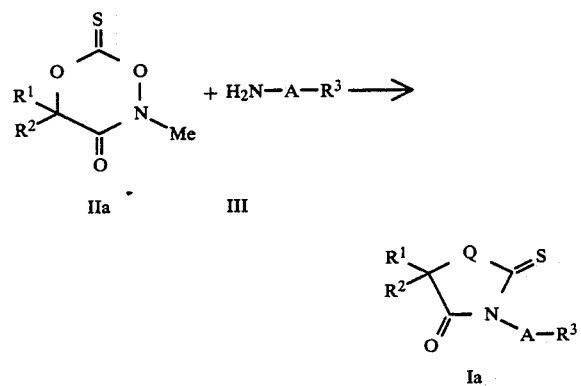

Treatment of thioxodioxazinones IIa with hydroxylamines (A=O) or hydrazines (A=NR$^4$) in an inert solvent such as methylene chloride, benzene, or THF at temperatures ranging from −10° C. to 35° C. gives the thioxooxazolidinones Ia. [Geffken, D.; Z. Naturforsch, 1983, 38b, 1008]

The thioxodioxazinones IIa are prepared according to the method outlined in Equation 3.

Equation 3

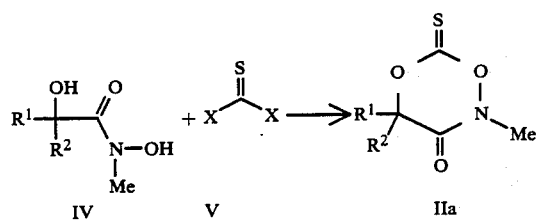

The hydroxamic acids IV are reacted with a thionoating agent V, such as thiophosgene (X=Cl) in the presence of a base or 1,1'-thiocarbonyldiimidazole (X=imidazole), to afford the thioxodioxazinones IIa. The reactions are performed at −20° C. to 25° C. in an inert solvent. [Geffken, D., Z. Naturforsch, 1983, 38b, 1008] The products are generally unstable at ambient temperature and therefore are reacted with the desired amine III immediately upon isolation.

Preparation of the hydroxylamines [Castellino, A. J.; Rapoport, H.; J. Org. Chem., 1984, 49, 1348] (III, A=O) and hydrazines [J. Timberlake; J. Stowell; The Chemistry of the Hydrazo, Azo, and Azoxy Groups (S. Patai, Ed.) John Wiley and Sons, Ltd., London (1975), p. 69; Demers, J. P.; Klaubert, D. J.; Tetrahedron Lett.. 1987, 4933] (III, A=NR$^4$) can be accomplished by literature methods by one skilled in the art.

The synthesis of the requisite hydroxamic acids IV can be accomplished by several known methods. As shown in Equation 4, the condensation of an α-hydroxycarboxylic acid VI (Z=H) with N-methylhydroxylamine hydrochloride affords the desired hydroxamic acids IV. [Geffken, D.; Kampf, H.; J. Chem. Ztg., 1979, 103, 19] Triethylamine is commonly used as an added base and 1,3-dicyclohexylcarbodiimide (DCC) is used as the dehydrating agent.

Equation 4

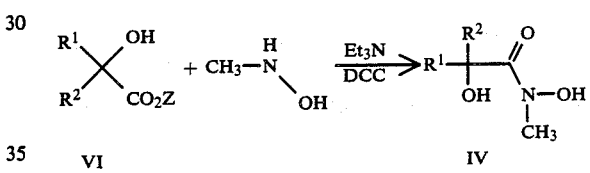

Many α-hydroxyacids VI are available from commercial sources. Others can be obtained by hydrolysis of the cyanohydrin derived from the corresponding ketone or aldehyde.

Alternative methods for producing the same types of compounds are known in the literature. As illustrated in Equation 5, α-hydroxyhydroxamic acids IV can also be synthesized by treating α-ketohydroxamic acids VII with an excess of a Grignard reagent. [Geffken, D.; Burchardt, A.; Arch. Pharm., 1988, 321, 311] The reactions are conducted in refluxing ether for 2 to 6 hours.

Equation 5

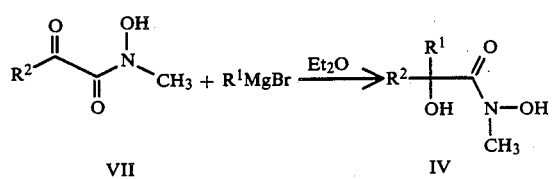

This procedure works best in cases where R$^2$ of the hydroxamic acids VII is a non-enolizable group, for example phenyl.

The α-ketohydroxamic acids VII can be prepared by condensing the glyoxylic acid chlorides VIII, derived from the corresponding carboxylic acids, [Geffken, D.; Burchardt, A.; Arch. Pharm., 1988, 321, 311] with O-trimethylsilyl-N-methylhydroxylamine [Geffken, D.; Burchardt, A.; Arch. Pharm., 1988, 321, 311] (Equation 6).

Equation 6

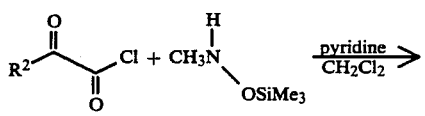

VIII

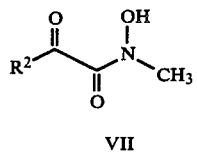

VII

These reactions are conducted in a mixture of pyridine and methylene chloride at 0° C. to 25° C.

The starting α-ketoacids VIII are either purchased from commercial sources or obtained by oxidation of the corresponding methyl ketone with selenium dioxide. [Hallmann, G.; Haegele, K.; *Annalen*, 1963, 662, 147]

A third method for producing α-hydroxyhydroxamic acids IV is specific to examples in which $R^1=R^2$ (IVa). This method, illustrated in Equation 7, involves adding an excess of Grignard reagent, typically five equivalents, to a solution of the hydroxamic acids IX in ether. [Geffken, D., *Arch. Pharm*, 1987, 320, 382] The reactions are normally performed at reflux.

Equation 7

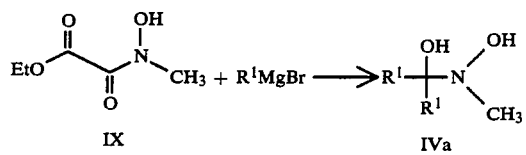

IX                IVa

The starting hydroxamic acids IX are prepared by treating ethyl oxalyl chloride X with N-methylhydroxylamine hydrochloride. Sodium carbonate is added as an acid scavenger (Equation 8). [Geffken, D., *Arch. Pharm.*, 1987, 321, 382]

Equation 8

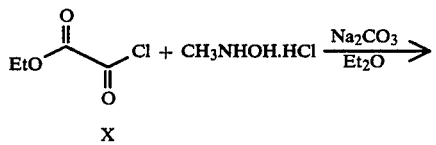

X

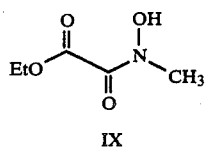

IX

A second and more expeditious route to compounds of Formula I in which Q is O, W is S, and A is $NR^4$ (Ib) is shown in Equation 9. This method involves sequential treatment of α-hydroxyesters VI (e.g. Z=methyl) with a base (e.g. potassium t-butoxide), carbon disulfide, an acylating agent (e.g. ethyl chloroformate), and finally a hydrazine. These reactions can be performed in inert solvents, for example THF, or neat at temperatures ranging from about 0° C. to 50° C. The intermediates need not be isolated and therefore the reaction can be conducted in one flask. A detailed discussion of this process is disclosed in copending application No. BA-8800.

Equation 9

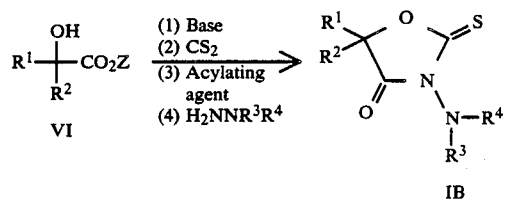

IB

The preparation of α-hydroxycarboxylic acids VI (Z=H) used to prepare the corresponding esters VI (e.g. Z=alkyl) is discussed above.

Compounds of general Formula I wherein Q, W, and A are all O (Ic) are prepared by the methods shown in Equation 10.

Equation 10

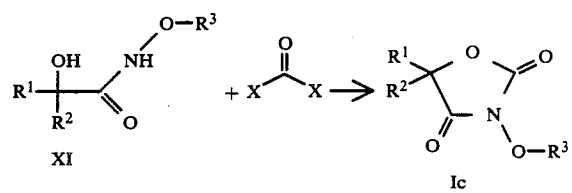

XI                Ic

The addition of a carbonylating agent, e.g. phosgene (X=Cl), 1,1'-thiocarbonyldiimidazole (X=imidazole), or oxalyl chloride, to hydroxamic acids of type XI produces dioxotetrahydrooxazoles Ic. The cyclizations can be conducted in an inert solvent, for example benzene or methylene chloride, at temperatures ranging from 0° C. to 80° C. Experimental details for reactions of this type have been reported as have the preparation of the starting hydroxamic acids XI. [Geffken, D.; Zinner, G.; *Chem. Ber.*, 1973, 106, 2246]

Compounds of Formula I in which Q and W are O and A is $NR^4$ (Id) are synthesized by treating hydroxamic acids IIb with various hydrazines, as illustrated in Equation 11. Depending on the nature of the substituents on IIb and the reacting hydrazine, the intermediate N-aminocarbamates XII may or may not be isolated. For cases in which ring closure is not spontaneous under the reaction conditions, treatment of XII with triethylamine in an inert solvent (such as THF) at temperatures ranging from 25° C. to 80° C. induces cyclization to Id. [Geffken, D.; *Arch. Pharm.*. 1982, 315, 802; Geffken, D. *Synthesis*. 1981, 38]

Equation 11

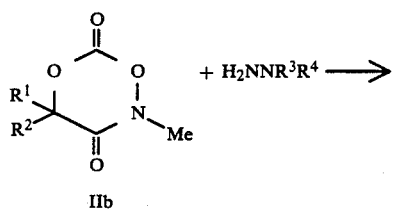

IIb

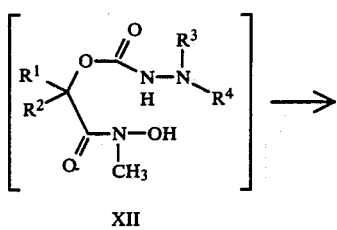

XII

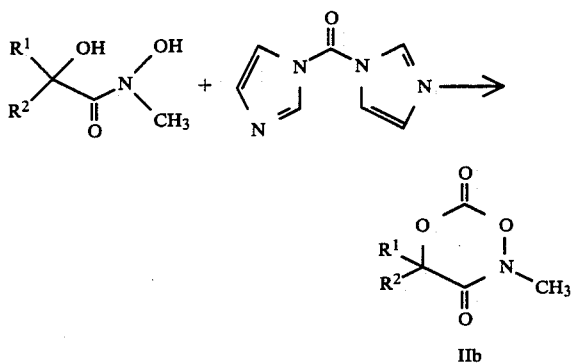

Id

The dioxazinediones IIb are readily prepared from the corresponding α-hydroxyhydroxamic acid by treatment with 1,1'-carbonyldiimidazole (Equation 12). The cyclization is performed in an inert solvent such as methylene chloride and is complete in less than one minute at 25° C. [Geffken, D.; *Arch. Pharm.*. 1982, 315, 802; Geffken, D., *Synthesis*, 1981, 38]

Equation 12

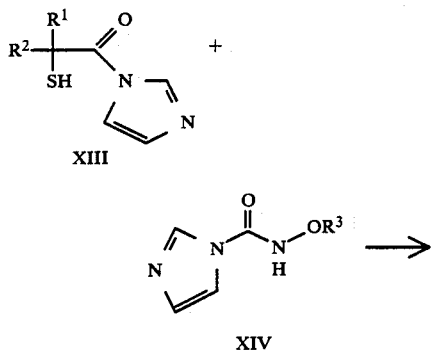

IIb

The preparation of compounds of Formula I where A and W are O and Q is S (Ie) follows directly from the teachings of Geffken, D. *Z. Naturforsch.* 1987, 42b, 1202. As shown in Equation 13, reaction of 2-mercaptoamides XIII with ureas of type XIV afford the thiazolidinediones Ie.

Equation 13

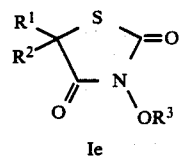

Ie

The starting acyl imidzoles XIII are readily synthesized by condensation of the corresponding carboxylic acids of 1,1'-carbonyldiimidazole. [Geffken, D. *Z. Naturforsch*, 1987, 42b, 1202] Mercaptocarboxylic acids have been prepared by several methods [Biilmann, E., *Ann. Chem.*, 1906, 348, 120; Bonner, W. A., *J. Org. Chem.*, 1968, 33, 1831] The preparaton of the ureas of Formula XIV as also disclosed in Geffken, D. *Z. Naturforsch*, 1987, 42b, 1202.

Compounds of Formula I wherein Q is S and A is $NR^4$ (If) are synthesized by the method shown in Equation 14.

Equation 14

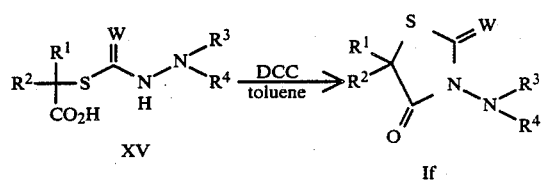

If

Treatment of carboxylic acids XV with 1,3-dicyclohexylcarbodiimide in an inert solvent (e.g. toluene) at 25° C. to 80° C. affords the thiazolidinediones (W=O) [Hanefield, W.; Jalili, M. A., *Arch. Pharm.*, 1987, 320; 367] and thioxothiazolidinones (W TM S) If.

The preparation of the precyclization substrates XV for the case in which W is O is discussed in the same article disclosing the cyclization. [Hanefield, W.; Jalili, M. A., *Arch. Pharm.*, 1987, 320, 367] The same procedure can also be applied to the preparation of the thioxothiazolidinones (W=S). As illustrated in Equation 15, the carboxylic acids Xv are obtained by treating α-bromocarboxylate salts XVI with XVII in water in the presence of a base, for example sodium carbonate. [Hanefield, W.; Jalili, M. A., *Arch. Pharm.*, 1987, 320, 367]

Equation 15

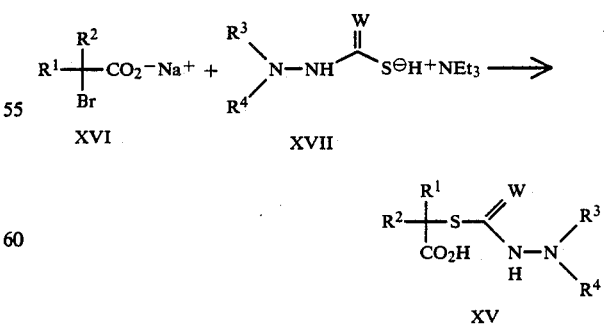

XV

In the case of the thiazolidinediones (If, W=O), the preparation of the carbazoylthiolates XVII from carbonyl sulfide, triethylamine, and various hydrazines is discussed in the literature. [Hanefield, W.; Jalili, M. A.,

*Arch. Pharm.*, 1987, 320, 367] The thioxothiazolidinones (If, W=S) can be prepared from the carbazoylthiolates XVIII (W=S) which are prepared in the same manner except carbon disulfide is used rather than carbonyl sulfide.

Tables I and II on the following pages show fungicidal compounds that can be advantageously prepared by the methods described above.

COMPOUND TABLES

TABLE 1

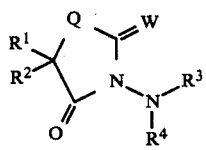

| EX # | Q | W | R¹ | R² | R³ | R⁴ | mp (°C.) |
|---|---|---|---|---|---|---|---|
| 1 | S | S | Me | Ph | Ph | H | |
| 2 | S | O | Me | Ph | Ph | H | |
| 3 | O | S | Me | Ph | Ph | H | 109 |
| 4 | O | O | Me | Ph | Ph | H | |
| 5 | O | S | H | Ph | Ph | H | 142 |
| 6 | O | S | Et | Ph | Ph | H | 96 |
| 7 | O | S | n-Hexyl | Ph | Ph | H | |
| 8 | O | S | CF₃ | Ph | Ph | H | |
| 9 | O | S | CF₃CH₂CH₂CH₂ | Ph | Ph | H | |
| 10 | O | S | cyclopropyl | Ph | Ph | H | 98 |
| 11 | O | S | cyclohexyl | Ph | Ph | H | |
| 12 | O | S | vinyl | Ph | Ph | H | 107 |
| 13 | O | S | allyl | Ph | Ph | H | 113 |
| 14 | O | S | acetylenyl | Ph | Ph | H | |
| 15 | O | S | propargyl | Ph | Ph | H | |
| 16 | O | S | methoxymethyl | Ph | Ph | H | |
| 17 | O | S | cyclopropylmethyl | Ph | Ph | H | |
| 18 | O | S | benzyl | Ph | Ph | H | 116 |
| 19 | O | S | 4'-methoxybenzyl | Ph | Ph | H | |
| 20 | O | S | 4'-nitrobenzyl | Ph | Ph | H | |
| 21 | O | S | 4'-trifluoromethylbenzyl | Ph | Ph | H | |
| 22 | O | S | 4'-methylbenzyl | Ph | Ph | H | |
| 23 | O | S | 2',4'-dichlorobenzyl | Ph | Ph | H | |
| 24 | O | S | 4'-fluorobenzyl | Ph | Ph | H | |
| 25 | O | S | Ph | Ph | Ph | H | |
| 26 | O | O | Ph | Ph | Ph | H | |
| 27 | O | S | 3-methoxyphenyl | 3-methoxyphenyl | Ph | H | 96 |
| 28 | O | O | 3-methoxyphenyl | 3-methoxyphenyl | Ph | H | 95 |
| 29 | O | S | 4-chlorophenyl | 4-chlorophenyl | Ph | H | 156 |
| 30 | O | O | 4-chlorophenyl | 4-chlorophenyl | Ph | H | 180 |
| 31 | O | S | 4-fluorophenyl | 4-fluorophenyl | phenyl | H | 152 |
| 32 | O | O | 4-fluorophenyl | 4-fluorophenyl | phenyl | H | 113 |
| 33 | O | S | 3-chlorophenyl | 3-chlorophenyl | 3-chlorophenyl | H | |
| 34 | O | O | 3-chlorophenyl | 3-chlorophenyl | 3-chlorophenyl | H | 136 |
| 35 | O | S | 3-chlorophenyl | 3-chlorophenyl | 4-methoxyphenyl | H | 99 |
| 36 | O | O | 3-chlorophenyl | 3-chlorophenyl | 4-methoxyphenyl | H | 109 |
| 37 | O | S | H | Me | Ph | H | 117 |
| 38 | O | S | H | t-Bu | Ph | H | 98 |
| 39 | O | S | H | i-Pr | Ph | H | 107 |
| 40 | O | S | H | cyclohexyl | Ph | H | 90 |
| 41 | O | S | H | benzyl | Ph | H | 141 |
| 42 | O | S | Me | Me | Ph | H | 132 |
| 43 | O | S | Me | benzyl | Ph | H | 99 |
| 44 | O | S | Me | phenoxymethyl | Ph | H | 77 |
| 45 | O | S | Me | n-Hexyl | Ph | H | |
| 46 | O | S | Me | 4-chlorophenyl | Ph | H | 156 |
| 47 | O | O | Me | 4-chlorophenyl | Ph | H | 116 |
| 48 | S | S | Me | 4-chlorophenyl | Ph | H | |
| 49 | S | O | Me | 4-chlorophenyl | Ph | H | |
| 50 | O | S | Me | 4-chlorophenyl | Ph | H | |
| 51 | O | S | Me | 2-chlorophenyl | Ph | H | |
| 52 | O | S | Me | 4-fluorophenyl | Ph | H | 150 |
| 53 | O | O | Me | 4-fluorophenyl | Ph | H | 102 |
| 54 | S | S | Me | 4-fluorophenyl | Ph | H | |
| 55 | S | O | Me | 4-fluorophenyl | Ph | H | |
| 56 | O | S | Me | 3-fluorophenyl | Ph | H | 108 |
| 57 | O | S | Me | 4-bromophenyl | Ph | H | |
| 58 | O | S | Me | 3,5-dichlorophenyl | Ph | H | |
| 59 | O | S | Me | 3,4-dichlorophenyl | Ph | H | 143 |
| 60 | O | S | Me | 2,4-difluorophenyl | Ph | H | |
| 61 | O | S | Me | 2-methylphenyl | Ph | H | |
| 62 | O | S | Me | 2,5-dimethylphenyl | Ph | H | |
| 63 | O | S | Me | 4-t-butylphenyl | Ph | H | |
| 64 | O | S | Me | 4-cyclohexylphenyl | Ph | H | 160 |
| 65 | O | S | Me | 3-trifluoromethylphenyl | Ph | H | |
| 66 | O | S | Me | 3-nonafluorobutyl- | Ph | H | |

TABLE 1-continued

| EX # | Q | W | R¹ | R² | R³ | R⁴ | mp (°C.) |
|---|---|---|---|---|---|---|---|
| | | | | phenyl | | | |
| 67 | O | S | Me | 4-methoxyphenyl | Ph | H | 156 |
| 68 | O | O | Me | 4-methoxyphenyl | Ph | H | 104 |
| 69 | O | S | Me | 4-n-pentyloxyphenyl | Ph | H | |
| 70 | O | S | Me | 4-allyloxyphenyl | Ph | H | |
| 71 | O | S | Me | 3-methylthiophenyl | Ph | H | |
| 72 | O | S | Me | 4-trifluoromethylthiophenyl | Ph | H | |
| 73 | O | S | Me | 4-trifluoromethoxyphenyl | Ph | H | |
| 74 | O | S | Me | 4-cyanophenyl | Ph | H | |
| 75 | O | S | Me | 4-phenoxyphenyl | Ph | H | 115 |
| 76 | O | O | Me | 4-phenoxyphenyl | Ph | H | |
| 77 | S | S | Me | 4-phenoxyphenyl | Ph | H | |
| 78 | S | O | Me | 4-phenoxyphenyl | Ph | H | |
| 79 | O | S | Me | 3-phenoxyphenyl | Ph | H | |
| 80 | O | O | Me | 3-phenoxyphenyl | Ph | H | |
| 81 | S | S | Me | 3-phenoxyphenyl | Ph | H | |
| 82 | S | O | Me | 3-phenoxyphenyl | Ph | H | |
| 83 | O | S | H | 3-(3,5-dichlorophenoxy)phenyl | Ph | H | 130 |
| 84 | O | S | H | 3-(3-trifluoromethylphenoxy)phenyl | Ph | H | |
| 85 | O | S | H | 3-phenoxyphenyl | Ph | H | 136 |
| 86 | O | S | Me | 4-(4-trifluoromethylphenoxy)phenyl | Ph | H | |
| 87 | O | S | Me | 4-(4-methoxyphenoxy)phenyl | Ph | H | |
| 88 | O | S | Me | 4-(2,4-dichlorophenoxy)phenyl | Ph | H | |
| 89 | O | S | Me | 4-methanesulfonylphenyl | Ph | H | |
| 90 | O | S | Me | 4-nitrophenyl | Ph | H | 170 |
| 91 | O | O | Me | 4-nitrophenyl | Ph | H | 116 |
| 92 | O | S | Me | 3-trifluoromethylphenyl | Ph | H | 134 |
| 93 | O | S | Me | 4-phenylthiophenyl | Ph | H | |
| 94 | O | S | Me | 4-phenylphenyl | Ph | H | 172 |
| 95 | O | S | Me | 2-naphthyl | Ph | H | 152 |
| 96 | O | S | Me | 1-naphthyl | Ph | H | |
| 97 | O | S | Me | 2-thienyl | Ph | H | |
| 98 | O | O | Me | 2-thienyl | Ph | H | |
| 99 | S | S | Me | 2-thienyl | Ph | H | |
| 100 | S | O | Me | 2-thienyl | Ph | H | |
| 101 | O | S | Me | 5-chloro-2-thienyl | Ph | H | |
| 102 | O | S | Me | 5-methyl-2-thienyl | Ph | H | |
| 103 | O | S | Me | 3-methoxy-2-thienyl | Ph | H | |
| 104 | O | S | Me | 3-thienyl | Ph | H | 121 |
| 105 | O | O | Me | 3-thienyl | Ph | H | |
| 106 | S | S | Me | 3-thienyl | Ph | H | |
| 107 | S | O | Me | 3-thienyl | Ph | H | |
| 108 | O | S | Me | 2,5-dichloro-3-thienyl | Ph | H | |
| 109 | O | S | Me | 2,5-dimethyl-3-thienyl | Ph | H | |
| 110 | O | S | Me | 2-phenoxy-3-thienyl | Ph | H | |
| 111 | O | S | Me | 2-nitro-4-thienyl | Ph | H | |
| 112 | O | S | Me | 3-methoxy-4-thienyl | Ph | H | |
| 113 | O | S | Me | 2-furyl | Ph | H | |
| 114 | O | S | Me | 3-furyl | Ph | H | |
| 115 | O | S | Me | 2-pyridyl | Ph | H | |
| 116 | O | S | Me | 3-pyridyl | Ph | H | |
| 117 | O | S | Me | 4-pyridyl | Ph | H | |
| 118 | O | S | —CH₂(CH₂)₃CH₂— | | Ph | H | oil |
| 119 | O | S | —CH₂(CH₂)₃CH₂— | | 3,5-dichlorophenyl | H | 184 |
| 120 | O | S | —CH₂CH₂NMeCH₂CH₂— | | Ph | H | |
| 121 | O | S | —CH₂CH₂SCH₂CH₂— | | Ph | H | |
| 122 | | | 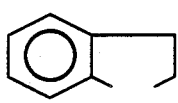 | | Ph | H | 168 |

TABLE 1-continued

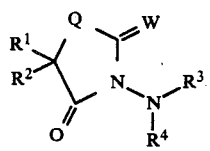

| EX # | Q | W | R¹ | R² | R³ | R⁴ | mp (°C.) |
|---|---|---|---|---|---|---|---|
| 123 | | | | | Ph | H | |
| 124 | | | | | Ph | H | |
| 125 | O | S | Me | 4-carbomethoxyphenyl | Ph | H | |
| 126 | O | S | Me | 4-benzylphenyl | Ph | H | |
| 127 | | | | | Ph | H | 189 |
| 128 | O | S | Me | Ph | 3,5-di-chlorophenyl | H | 142 |
| 129 | O | S | cyclopropyl | Ph | 3,5-di-chlorophenyl | H | 133 |
| 130 | O | S | Me | phenoxymethyl | 3,5-dichlorophenyl | H | 146 |
| 131 | O | S | Me | Ph | 2,6-dichlorophenyl | H | 157 |
| 132 | O | S | Me | 4-phenoxyphenyl | 2,6-dichlorophenyl | H | 118 |
| 133 | O | S | Me | phenoxymethyl | 2,6-dichlorophenyl | H | 122 |
| 134 | O | S | H | t-Bu | 2,6-dichlorophenyl | H | 87 |
| 135 | O | S | Me | Ph | 4-fluorophenyl | H | 72 |
| 136 | O | O | Me | Ph | 4-fluorophenyl | H | |
| 137 | S | S | Me | Ph | 4-fluorophenyl | H | |
| 138 | O | S | Me | 4-fluorophenyl | 4-fluorophenyl | H | 91 |
| 139 | O | S | Me | 4-cyclohexylphenyl | 4-fluorophenyl | H | 155 |
| 140 | O | S | Me | phenylthiomethyl | 4-fluorophenyl | H | |
| 141 | O | S | Me | phenylthiomethyl | 4-fluorophenyl | H | 68 |
| 142 | O | S | Me | Ph | 3-fluorophenyl | H | |
| 143 | O | S | Me | Ph | 4-chlorophenyl | H | |
| 144 | O | S | Me | Ph | 3-chlorophenyl | H | 132 |
| 145 | O | O | Me | Ph | 3-chlorophenyl | H | 59 |
| 146 | O | O | Me | 4-methoxyphenyl | 3-chlorophenyl | H | 152 |
| 147 | O | S | Me | Ph | 2-fluorophenyl | H | |
| 148 | O | S | Me | Ph | 2,5-difluorophenyl | H | oil |
| 149 | O | S | Me | Ph | 4-methylphenyl | H | 142 |
| 150 | O | S | Me | 4-fluorophenyl | 4-methylphenyl | H | |
| 151 | O | S | Me | 4-phenoxyphenyl | 4-methylphenyl | H | 146 |
| 152 | O | O | Me | 4-phenoxyphenyl | 4-methylphenyl | H | |
| 153 | O | S | Me | phenylthiomethyl | 4-methylphenyl | H | 89 |
| 154 | O | S | Me | phenoxymethyl | 4-methylphenyl | H | 155 |
| 155 | O | S | Me | Ph | 2,6-dimethylphenyl | H | 101 |
| 156 | O | S | Me | Ph | 4-t-butylphenyl | H | 125 |
| 157 | O | S | Me | Ph | 3-methylphenyl | H | |
| 158 | O | S | Me | Ph | 2-methylphenyl | H | |
| 159 | O | S | Me | Ph | 4-methoxyphenyl | H | 135 |
| 160 | O | O | Me | Ph | 4-methoxyphenyl | H | 134 |
| 161 | O | S | Me | Ph | 4-n-pentyloxyphenyl | H | oil |
| 162 | O | S | Me | Ph | 4-allyloxyphenyl | H | |
| 163 | O | S | Me | Ph | 4-trifluoromethylphenyl | H | |
| 164 | O | S | Me | Ph | 3-trifluoromethylphenyl | H | |
| 165 | O | S | Me | Ph | 4-methylthiophenyl | H | |
| 166 | O | S | Me | Ph | 4-methanesulfonylphenyl | H | |
| 167 | O | S | Me | Ph | 4-nitro | H | |
| 168 | O | S | Me | Ph | 4-cyano | H | |
| 169 | O | S | Me | Ph | 4-carbomethoxy | H | |
| 170 | O | S | Me | Ph | benzyl | H | |
| 171 | O | S | Me | Ph | 2-thienyl | H | |
| 172 | O | S | Me | Ph | 3-furyl | H | |
| 173 | O | S | Me | Ph | 2-pyridyl | H | 147 |
| 174 | O | S | Me | Ph | 5-trifluoromethyl-2-pyridyl | H | 150 |
| 175 | O | S | Me | Ph | 2-pyrimidyl | H | 187 |
| 176 | O | S | Me | Ph | 6-chloro-3-pyridazyl | H | 184 |
| 177 | O | S | Me | Ph | ethyl | H | |
| 178 | O | S | Me | Ph | cyclohexyl | H | |

TABLE 1-continued

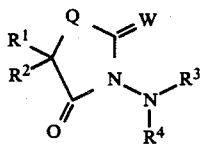

| EX # | Q | W | R¹ | R² | R³ | R⁴ | mp (°C.) |
|---|---|---|---|---|---|---|---|
| 179 | O | S | Me | Ph | t-Bu | H | 48 |
| 180 | O | S | Me | Ph | n-decyl | H | |
| 181 | O | S | Me | Ph | Ph | formyl | |
| 182 | O | S | Me | Ph | Ph | acetyl | 96 |
| 183 | O | S | Me | Ph | Ph | trifluoroacetyl | 62 |
| 184 | O | S | Me | Ph | Ph | methoxyacetyl | oil |
| 185 | O | S | Me | Ph | Ph | methoxycarbonyl | |
| 186 | O | S | Me | Ph | Ph | methylaminocarbonyl | |
| 187 | O | S | Me | Ph | Ph | methanesulfonyl | |
| 188 | O | S | Me | Ph | Ph | methyl | |
| 189 | O | S | Me | 3-thienyl | Ph | methyl | |
| 190 | O | S | 4-flurorphenyl | Ph | Ph | methyl | |
| 191 | O | S | 4-phenoxyphenyl | Ph | Ph | methyl | |
| 192 | O | S | Me | Ph | Ph | methyl | |
| 193 | O | O | Me | Ph | Ph | methyl | |
| 194 | S | S | Me | Ph | Ph | methyl | |
| 195 | S | O | Me | Ph | Ph | methyl | |
| 196 | O | S | Me | Ph | Ph | phenylaminocarbonyl | |
| 197 | O | S | Me | Ph | Ph | allyl | |
| 198 | O | S | Me | Ph | Ph | propargyl | |
| 199 | O | S | Me | Ph | Ph | cyclobutyl | |
| 200 | O | S | me | Ph | Ph | benzyl | |
| 201 | O | S | Me | Ph | —CH₂CH₂CH₂CH₂CH₂CH₂— | | 83 |
| 202 | O | S | Me | Ph | | | |

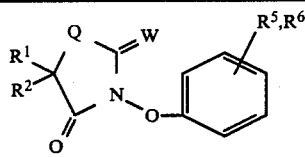

TABLE 2

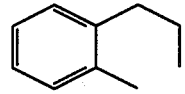

| EX # | Q | W | R¹ | R² | R⁵ | R⁶ | mp (°C.) |
|---|---|---|---|---|---|---|---|
| 202 | O | S | Me | Ph | H | H | |
| 203 | O | O | Me | Ph | H | H | |
| 204 | S | S | Me | Ph | H | H | |
| 205 | S | O | Me | Ph | H | H | |
| 206 | O | S | H | Ph | H | H | |
| 207 | O | S | trifluoromethyl | Ph | H | H | |
| 208 | O | S | Me | 3-thienyl | H | H | |
| 209 | O | S | Me | 4-fluorophenyl | H | H | |
| 210 | O | S | Me | 4-phenoxyphenyl | H | H | |
| 211 | O | S | Me | 3-trifluoromethylphenyl | H | H | |
| 212 | O | S | Me | Ph | 4-fluoro | H | |
| 213 | O | S | Me | Ph | 3-trifluoromethyl | H | |
| 214 | O | S | Me | Ph | 4-phenoxy | H | |
| 215 | O | S | Me | Ph | 2-chloro | 4-chloro | |
| 216 | O | S | Me | Ph | 2-Me | 6-Me | |

Formulation

The compounds of this invention will generally be used in formulation with a liquid or solid diluent or with an organic solvent. Useful formulations of the compounds of Formula I can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of (a) about 0.1% to 35% surfactant(s) and (b) about 5% to 99% solid or liquid inert diluent(s). More specifically, they will contain these ingredients in the following approximate proportions:

|  | Active Ingredient | Percent by Weight Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 5–50 | 40–95 | 0–35 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al.. "Handbook of Insecticide Dust Diluents and Carriers", 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 2 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17 and Examples 1–4.

G. C. Klingman, "Weed Control as a Science", John Wiley and Sons, Inc., New York, 1961, pp. 81–96.

J. D. Fryer and S. A. Evans, "Weed Control Handbook", 5th Edn. Blackwell Scientific Publications, Oxford, 1968, pp. 101–103.

Examples of useful formulations of compounds of the present invention are as follows.

EXAMPLES

EXAMPLE 217

Wettable Powder

| | |
|---|---|
| 5-methyl-5-phenyl-3-(phenylamino)-2-thioxo-4-oxazolidinone | 80% |
| Sodium Alkylnaphthalenesulfonate | 4% |
| Sodium Ligninsulfonate | 2% |
| Synthetic Amorphous Silica | 1% |
| Kaolinite | 13% |

The ingredients are blended, hammermilled, reblended and packaged.

EXAMPLE 218

High Strength Concentrate

| | |
|---|---|
| 5-methyl-5-phenyl-3-(phenylamino)-2-thioxo-4-oxazolidinone | 98.5% |
| Silica Aerogel | 0.5% |
| Synthetic Amorphous Silica | 1.0% |

The ingredients are blended and ground in a hammermill to produce a high strength concentrate essentially all passing a U.S.S. No. 50 Sieve (0.3 mm openings). This material may then be formulated in a variety of ways.

EXAMPLE 219

Solution

| | |
|---|---|
| 5-methyl-5-phenyl-3-(phenylamino)-2-thioxo-4-oxazolidinone | 25% |
| N-methyl-2-pyrrolidone | 75% |

The ingredients are combined and stirred to produce a solution, which can be used for low volume applications.

EXAMPLE 220

Emulsifiable Concentrate

| | |
|---|---|
| 5-methyl-5-phenyl-3-(phenylamino)-2-thioxo-4-oxazolidinone | 15% |
| Blend of calcium sulfonates and non-ionic surfactants | 6% |
| Acetophenone | 79% |

The ingredients are combined and stirred until the active is dissolved. A fine screen filter is included in packaging operation to insure the absence of any extraneous undissolved material in the product.

Utility

The compounds of this invention are useful as plant disease control agents. They provide control of diseases caused by a broad spectrum of plant pathogens in the basidiomycete, and ascomycete classes and particularly against fungi in the oomycete class. They are effective in controlling a broad spectrum of plant diseases, particularly foliar pathogens of ornamental, vegetable, field, cereal and fruit crops, such as *Plasmopara viticola, Phytophthora infestans, Peronospora tabacina, Pseudperonospora cubensis, Phytophthora megasperma, Botrytis cinerea, Venturia inaequalis, Puccinia recondita, Pythium aphanidermatum, Alternaria brassicola, Septoria nodorum, Cercosporidium personatum* and species related to these pathogens.

The compounds of this invention can be mixed with fungicides, bactericides, acaricides, nematicides, insecticides or other biologically active compounds in order to achieve desired results with a minimum of expenditure of time, effort and material. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalamide (captan)
N-trichloromethylthiophthalimide (folpet)
dimethyl 4,4'-(o-phenylene)bis(3-thioallophanate) (thiophanate-methyl)
2-(thiazol-4-yl)benzimidazole (thiabendazole)
aluminum tri(O-ethyl phosphonate)(phosethyl aluminum)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[1,1,2,2-tetrachloroethyl)thio]cyclohex-4-ene1,2-dicarbioximide (captafol)
3-(3,5-dichlorophenyl)-N-(1-methylethyl)-2,4-dioxo-1imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)
4-(3-(4-(1,1-dimethyl-ethyl)phenyl)-2-methyl)propyl-2,6-dimethylmorpholine (Fenpropimorph)
4-(3-4(1,1-dimethyl-ethyl)phenyl)-2methyl)propyl-piperidine (Fenpropidine)
Bayleton ® 1-(4-chlorophenoxy)-3,3-dimethyl-1-(1H1,2,4- triazol-1-yl)butane
Systhane ® 2-(4-chlorophenyl)-2-(1H-1,2,4-triazol-1yl-methyl)hexanenitrile Folicur ® (tebuconazol)
Score ® 3-chloro-4-[4-methyl-2-(1H-1,2,4-triazol)-1-ylmethyl]-1,3-dioxolan-2-yl]phenyl-4-chlorophenyl ether
Topaz ® 1-[2-(2,4-dichlorophenyl)pentyl]1H-1,2,4triazole
Impact ® (±)-α-(2-fluorophenyl-α-(4-fluorophenyl)-1H1,2,4-triazole-1-ethanol
Nustar ® 1-[[bis(4-fluorophenyl)methylsilyl]methyl]-1H-1,2,4-triazole
Sportak ® 1-N-propyl-N-[2(2,4,6-trichlorophenoxy)ethyl]carbamoylimidazole
Tilt ® 1-[[2-(2,4-dichlorophenyl)-4-propyl-1,3-di-oxolan-2-yl]methyl]-1H-1,2,4-triazole
Rubigan ® α-(2-chlorophenyl-α-(4-chlorophenyl)-5pyridinemethanol
copper oxychloride furalaxyl methyl N-(2,6-dimethylphenyl)-N-(2-furanylcarbonyl)-DL-alaninate
Anvil ® (hexaconazole)

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3-B]quinonolin-2-one (oxythioquinox)
2,2,2-trichloro-1,1-bis(4-chlorophenyl)ethanol (dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematicides

2-[diethoxyphosphinylimino]-1,3-diethietane (fosthietan)
S-methyl-1-(dimethylcarbamoyl)-N-(methylcarbamoyloxy)thioformimidate (oxamyl)
S-methyl-1-carbamoyl-N-(methylcarbamoyloxy)thioformimidate
N-isopropylphosphoramidic acid, O-ethyl-O'-[4-(methyl- thio)-m-tolyl]diester (fenamiphos)

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-P-nitrophenyl ester (methyl parathion)
methylcarbamic acid, ester with α-naphthol (carbaryl)
methyl N-[[(methylamino)carbonyl]oxy]ethanimidothioate (methomyl)
N -(4-chloro-o-tolyl)-N,N-dimethylformamidine (chlorodimeform)
O,O-diethyl-O-(2-isopropyl-4-methyl-6-pyrimidyl)-phosphorothioate (diazinon)
octachlorocamphene (toxaphene)
O-ethyl O-P-nitrophenyl phenylphosphonothioate (EPN)
cyano(3-phenoxyphenyl)-methyl 4-chloro-α-(1-methylethyl)benzeneacetate (fenvalerate)
(3-phenoxyphenyl)methyl (±)-cis,trans-3-(2,2-dichloroethenyl)-2,2-dimethylcyclopropanecarboxylate (permethrin)
dimethyl N,N'-[thiobis(N-methylimmo)carbonyloxy]]-bis[ethanimidothioate) (thiodicarb)
phosphorothiolothionic acid, O-ethyl-O-[4-(methylthio)phenyl]-S-n-propyl ester (sulprofos)
α-cyano-3-phenoxybenzyl 3-(2,2-dichlorovinyl)-2,2-dimethylcyclopropanecarboxylate (cypermethrin)
cyano(3-phenoxyphenyl)methyl 4-(difluoromethoxy)-α-(methylethyl)benzeneacetate (flucythrinate)
O,O-diethyl-O-(3,5,6-trichloro-2-pyridyl)phosphorothioate (chlorpyrifos)
O,O-dimethyl-S-[(4-oxo-1,2,3-benzotriazin-3-(4H)-yl)methyl]phosphorodithioate (azinphos-methyl)

5,6-dimethyl-2-dimethylamino-4-pyrimidinyl dimethyl carbamate (pirimicarb)

S-(N-formyl-N-methylcarbamoylmethyl)-O,O-dimethyl phosphorodithioate (formothion)

S-2-(ethylthioethyl)-O,O-dimethyl phosphiorothioate (demeton-S-methyl)

α-cyano-3-phenoxybenzyl cis-3(2,2-dibromovinyl)-2,2-dimethylcyclopropane carboxylate (deltamethrin)

cyano(3-phenoxyphenyl)methyl ester of N-(2-chloro-4-trifluoromethylphenyl)alanine (fluvalinate)

Application

Disease control is ordinarily accomplished by applying an effective amount of the compound either pre- or post-infection to the portion of the plant to be protected such as the roots, stems, foliage, fruit, seeds, tubers or bulbs. The compound may also be applied to the seed from which the plants to be protected are to be grown.

Rates of application for these compounds can be influenced by many factors of the environment and should be determined under actual use conditions. Foliage can normally be protected when treated at a rate of from less than 1 g/ha to 10,000 g/ha of active ingredient. Seed and seedlings can normally be protected when seed is treated at a rate of from 1 to 10 grams per kilogram of seed.

EXAMPLE A

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on apple seedlings. The following day the seedlings were inoculated with a spore suspension of *Venturia inaequalis* (the causal agent of apple scab) and incubated in a saturated atmosphere at 20° C. for 24 hr, and then moved to a growth chamber at 22° C. for 11 days, after which disease ratings were made.

EXAMPLE B

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on peanut seedlings. The following day the seedlings were inoculated with a spore suspension of *Cercosporidium personatum* (the causal agent of peanut late leafspot) and incubated in a saturated atmosphere at 22° C. for 24 hr, a high humidity atmosphere at 22 to 30° C. for 5 days, and then moved to a growth chamber at 29° C. for 6 days, after which disease ratings were made.

EXAMPLE C

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 hr, and then moved to a growth chamber at 20° C. for 6 days, after which disease ratings were made.

EXAMPLE D

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 hr, and then moved to a growth chamber at 20° C. for 5 days, after which disease ratings were made.

EXAMPLE E

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 hr, moved to a growth chamber at 20° C. for 6 days, and then incubated in a saturated atmosphere at 20° C. for 24 hr, after which disease ratings were made.

EXAMPLE F

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 hr, and moved to a growth chamber at 20° C. for 5 days, after which disease ratings were made.

EXAMPLE G

The test compounds were dissolved in acetone in an amount equal to 3% of the final volume and then suspended at a concentration of 1000 ppm in purified water containing 250 ppm of the surfactant Trem 014 (polyhydric alcohol esters). This suspension was sprayed to the point of run-off on tobacco seedlings. The following day the seedlings were inoculated with a spore suspension of *Peronospora tabacina* (the causal agent of tobacco blue mold) and incubated in a saturated atmosphere at 20° C. for 24 hr, moved to a growth chamber at 22° C. for 6 days, and then incubated in a saturated atmosphere at 20° C. for 24 hr, after which disease ratings were made.

EXAMPLE H

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on cucumber seedlings. The following day the seedlings were inoculated with a spore suspension of *Pseudoperonospora cubensis* (the causal agent of cucumber downy mildew) and incubated in a saturated atmosphere at 20° C. for 24 hr, moved to a growth chamber at 20° C. for 6 days, and the incubated in a saturated atmosphere at 20° C. for 24 hr, after which disease ratings were made.

Examples which further illustrate the invention can be found in the following tables (Tables 3 to 5). In the table, a rating of 100 indicates 100% disease control and a rating of 0 indicates no disease control (relative to the carrier sprayed controls). A "-" indicates that no test was performed at that concentration on that disease.

TABLE 3

UNREPLICATED TEST DATA AT 200 PPM

| EX # | EX. A | EX. B | EX. D | EX. F |
|------|-------|-------|-------|-------|
| 135  | 64    | 71    | 64    | 0     |
| 122  | 39    | 43    | 77    | 96    |
| 179  | 50    | 0     | 0     | 0     |
| 175  | —     | —     | 76    | 0     |
| 174  | —     | —     | 0     | 0     |
| 3    | 59    | 91    | 99    | —     |
| 42   | 77    | 23    | 0     | 0     |
| 27   | 0     | 0     | 0     | 0     |
| 46   | 61    | 79    | 93    | 0     |
| 47   | 39    | 23    | 0     | 0     |
| 52   | 88    | 23    | 99    | 0     |
| 53   | 11    | 23    | 93    | 0     |
| 67   | 61    | 58    | 64    | 0     |
| 68   | 11    | 23    | 86    | 0     |
| 90   | 61    | 23    | 64    | 0     |
| 91   | 39    | 23    | 0     | 0     |
| 29   | 61    | 23    | 0     | 0     |
| 30   | 77    | 23    | 0     | 0     |
| 31   | 39    | 0     | 0     | 0     |
| 32   | 39    | 0     | 0     | 0     |
| 28   | 39    | 0     | 0     | 0     |
| 33   | 11    | 0     | 0     | 0     |
| 34   | 61    | 0     | 0     | 0     |
| 25   | 11    | 23    | 0     | 0     |
| 26   | 39    | 23    | 0     | 0     |
| 144  | 39    | 23    | 86    | 0     |
| 145  | 61    | 23    | 0     | 0     |
| 159  | 11    | 23    | 0     | 0     |
| 160  | 61    | 23    | 0     | 0     |
| 43   | 39    | 0     | 0     | 0     |
| 75   | 61    | 23    | 26    | 0     |
| 146  | 61    | 0     | 0     | 0     |
| 35   | 61    | 0     | 0     | 0     |
| 36   | 61    | 23    | 0     | 0     |
| 4    | 39    | 23    | 47    | 0     |
| 104  | 0     | 43    | 99    | 88    |
| 118  | 6     | 0     | 47    | 35    |
| 119  | 0     | 0     | 0     | 0     |
| 39   | 0     | 0     | 0     | 96    |
| 38   | 64    | 0     | 0     | 88    |
| 5    | 39    | 0     | 47    | 99    |
| 40   | 81    | 0     | 26    | 79    |
| 41   | 81    | 0     | 0     | 35    |
| 182  | 39    | 94    | 26    | 35    |
| 18   | 39    | 0     | 0     | 63    |
| 188  | 6     | 43    | 77    | 0     |
| 128  | 39    | 43    | 0     | 0     |
| 6    | 81    | 0     | 0     | 0     |
| 10   | 6     | 43    | 0     | 0     |
| 129  | 39    | 0     | 0     | 35    |

TABLE 4

UNREPLICATED TEST DATA AT 200 PPM

| EX # | EX. A | EX. B | EX. C |
|------|-------|-------|-------|
| 3    | —     | 92    | 100   |
| 75   | 56    | —     | —     |

TABLE 5

REPLICATED TEST DATA AT THE SPECIFIED RATE

| EX # | PPM | EX. D | EX. E | EX. G | EX. H |
|------|-----|-------|-------|-------|-------|
| 135  | 200 | 97    | 100   | —     | —     |
| 135  | 40  | 47    | 100   | —     | —     |
| 3    | 200 | 100   | 100   | —     | —     |
| 3    | 40  | 98    | 100   | 100   | 100   |
| 42   | 200 | 25    | —     | —     | —     |
| 42   | 40  | 0     | 17    | —     | —     |
| 27   | 200 | 0     | —     | —     | —     |
| 27   | 40  | 0     | 61    | —     | —     |
| 46   | 200 | 88    | —     | —     | —     |
| 46   | 40  | 91    | 97    | 98    | 79    |
| 47   | 200 | 76    | —     | —     | —     |
| 47   | 40  | 8     | 88    | 62    | 67    |
| 52   | 200 | 100   | —     | —     | —     |
| 52   | 40  | 98    | 100   | 100   | 100   |
| 53   | 200 | 92    | —     | —     | —     |
| 53   | 40  | 67    | 99    | 99    | 100   |
| 67   | 200 | 88    | —     | —     | —     |
| 67   | 40  | 67    | 100   | 55    | 62    |
| 68   | 200 | 15    | —     | —     | —     |
| 68   | 40  | 25    | 75    | —     | —     |
| 90   | 200 | 82    | —     | —     | —     |
| 90   | 40  | 52    | 25    | —     | —     |
| 91   | 200 | 17    | —     | —     | —     |
| 91   | 40  | 0     | 32    | —     | —     |
| 29   | 200 | 15    | —     | —     | —     |
| 29   | 40  | 8     | 24    | —     | —     |
| 30   | 200 | 17    | —     | —     | —     |
| 30   | 40  | 0     | 32    | —     | —     |
| 31   | 200 | 8     | —     | —     | —     |
| 31   | 40  | 8     | 65    | —     | —     |
| 32   | 200 | 0     | —     | —     | —     |
| 32   | 40  | 17    | 80    | —     | —     |
| 28   | 200 | 0     | —     | —     | —     |
| 28   | 40  | 8     | 72    | —     | —     |
| 33   | 200 | 0     | —     | —     | —     |
| 33   | 40  | 8     | 32    | —     | —     |
| 34   | 200 | 15    | —     | —     | —     |
| 34   | 40  | 0     | 42    | —     | —     |
| 25   | 200 | 0     | —     | —     | —     |
| 25   | 40  | 0     | 24    | —     | —     |
| 26   | 200 | 0     | —     | —     | —     |
| 26   | 40  | 8     | 17    | —     | —     |
| 144  | 200 | 94    | —     | —     | —     |
| 144  | 40  | 57    | 97    | —     | —     |
| 145  | 200 | 62    | —     | —     | —     |
| 145  | 40  | 39    | —     | —     | —     |
| 159  | 200 | 0     | —     | —     | —     |
| 159  | 40  | 17    | 73    | —     | —     |
| 160  | 200 | 8     | —     | —     | —     |
| 160  | 40  | 0     | 0     | —     | —     |
| 43   | 200 | 0     | —     | —     | —     |
| 43   | 40  | 0     | 49    | —     | —     |
| 75   | 200 | 91    | 100   | —     | —     |
| 75   | 40  | 65    | 100   | 100   | 100   |
| 146  | 200 | 0     | —     | —     | —     |
| 146  | 40  | 0     | 34    | —     | —     |
| 35   | 200 | 0     | —     | —     | —     |
| 35   | 40  | 0     | 15    | —     | —     |
| 36   | 200 | 0     | —     | —     | —     |
| 36   | 40  | 0     | 17    | —     | —     |
| 4    | 200 | 88    | —     | —     | —     |
| 4    | 40  | 52    | 98    | 97    | 100   |
| 104  | 200 | 100   | 100   | —     | —     |
| 104  | 40  | 71    | 100   | 92    | 89    |
| 118  | 200 | 84    | 100   | —     | —     |
| 118  | 40  | 8     | 48    | 0     | 0     |
| 119  | 200 | 0     | 78    | —     | —     |
| 119  | 40  | 16    | 15    | 0     | 0     |
| 39   | 200 | 16    | 48    | —     | —     |
| 39   | 40  | 0     | 23    | 0     | 0     |
| 38   | 200 | 0     | 86    | —     | —     |
| 38   | 40  | 8     | —     | 0     | 11    |
| 5    | 200 | 86    | 100   | —     | —     |
| 5    | 40  | 8     | 97    | 0     | 25    |
| 40   | 200 | 52    | 68    | —     | —     |
| 40   | 40  | 0     | 15    | 0     | 6     |
| 41   | 200 | 8     | 71    | —     | —     |
| 41   | 40  | 0     | —     | 0     | 6     |
| 182  | 200 | 23    | 96    | —     | —     |

TABLE 5-continued

| | | REPLICATED TEST DATA AT THE SPECIFIED RATE | | | |
|---|---|---|---|---|---|
| EX # | PPM | EX. D | EX. E | EX. G | EX. H |
| 182 | 40 | 0 | 45 | 13 | 11 |
| 18 | 200 | 21 | 93 | — | — |
| 18 | 40 | 0 | 79 | 0 | 39 |
| 188 | 200 | 65 | 100 | — | — |
| 188 | 40 | 16 | 82 | 32 | 46 |
| 128 | 200 | 15 | 100 | — | — |
| 128 | 40 | 0 | 89 | 0 | 11 |
| 6 | 200 | 33 | 100 | — | — |
| 6 | 40 | 0 | — | 0 | 0 |
| 10 | 200 | 0 | 100 | — | — |
| 10 | 40 | 8 | 77 | 0 | 0 |
| 129 | 200 | 0 | 100 | — | — |
| 129 | 40 | 0 | 58 | 0 | 6 |

What is claimed is:

1. A method of controlling fungus disease in plants that comprise treating the locus to be protected with a fungicidally amount of a compound of Formula I,

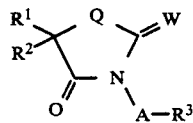

wherein:
A is $NR^4$,
Q is O,
W is O or S,
$R^1$ is H, $C_1$ to $C_6$ alkyl, $C_1$ to $C_6$ haloalkyl, $C_3$ to $C_6$ cycloalkyl, $C_2$ to $C_6$ alkenyl, $C_2$ to $C_6$ alkynyl, $C_2$ to $C_6$ alkoxyalkyl, $C_1$ to $C_3$ alkyl substituted with $C_3$ to $C_6$ cycloalkyl,
  phenyl or benzyl, wherein said phenyl or benzyl ring is substituted on the ring with $R^6$, and the benzylic carbon is substituted with $R^7$;
$R^2$ is phenyl substituted with $R^5$ and $R^6$, naphthyl substituted with 1 to 2 groups selected from $R^6$,
$C_1$ to $C_2$ alkyl substituted with phenoxy or phenylthio, said phenoxy or phenylthio being substituted on the ring with $R^6$,
$C_1$ to $C_6$ alkyl; or
$R^3$ is phenyl substituted with $R^5$ and $R^6$, benzyl substituted on the benzylic carbon with a group selected from $R^7$ and substituted on the phenyl ring with $R^6$, naphthyl substituted with $R^6$,
$R^4$ is hydrogen, formyl, $C_2$ to $C_4$ alkylcarbonyl, $C_2$ to $C_4$ haloalkylcarbonyl, $C_2$ to $C_4$ alkoxyalkylcarbonyl, $C_2$ to $C_4$ alkoxycarbonyl, $C_2$ to $C_5$ alkylaminocarbonyl, $C_1$ to $C_4$ alkylsulfonyl, $C_1$ to $C_6$ alkyl, $C_4$ to $C_6$ cycloalkyl, benzyl substituted with $R^6$ on the phenyl ring and substituted with $R^7$ on the benzylic carbon, phenylaminocarbonyl where said phenyl is substituted with $R^6$, $C_3$ to $C_4$ alkenyl, $C_3$ to $C_4$ alkynyl; or
$R^5$ is hydrogen, halogen, $C_1$ to $C_6$ alyl, $C_1$ to $C_6$ haloalkyl, $C_1$ to $C_6$ alkoxy, $C_3$ to $C_4$ alkenyloxy, $C_1$ to $C_5$ alkylthio, $C_1$ to $C_4$ haloalkylthio, $C_1$ to $C_4$ haloalkoxy, $C_1$ to $C_4$ alkylsulfonyl, $C_1$ to $C_4$ haloalkylsulfonyl, nitro, phenyl substituted with $R^6$, phenoxy substituted with $R^6$, phenylthio substituted with $R^6$, cyano, $C_3$ to $C_4$ alkynyloxy, $C_2$ to $C_6$ alkoxyalkyl, $C_2$ to $C_6$ alkoxyalkyoxy, phenoxymethyl substituted on the phenyl ring with $R^6$, benzyloxy substituted on the phenyl ring with $R^6$, phenethyloxy substituted on the phenyl ring with $R^6$, phenethyl substituted on the phenyl ring with $R^6$ or benzyl substituted on the phenyl ring with $R^6$, phenoxy substituted with $R^6$, $C_2$ to $C_6$ carboalkoxy, $C_5$ to $C_6$ cycloalkyl;
$R^6$ is hydrogen, 1 to 2 halogen, methyl, trifluoromethyl, $C_1$ to $C_4$ alkoxy, methylthio and nitro.

2. The method claim 1 wherein W is sulfur.

3. The method of claim 2 wherein:
$R_1$ is $C_1$ to $C_4$ alkyl, $C_1$ to $C_4$ haloalkyl, $C_3$ to $C_4$ cycloalkyl, $C_2$ to $C_4$ alkenyl, $C_2$ to $C_4$ alkynyl, $C_2$ to $C_4$ alkoxyalkyl;
$R^2$ is phenyl substituted with $R^5$ and $R^6$, naphthyl substituted with $R^6$, and
$R^3$ is phenyl substituted with $R^5$ and $R^6$.

4. The method of claim 3 wherein:
$R_1$ is $C_1$ to $C_4$ alkyl, $CF_3$, $C_2$ to $C_3$ alkenyl, $C_2$ to $C_3$ alkynyl;
$R^2$ is phenyl substituted with $R^5$ and $R^6$,
$R^3$ is phenyl substituted with $R^5$ and $R^6$;
$R^4$ is hydrogen, $C_1$ to $C_4$ alkyl;
$R^5$ is hydrogen, halogen, $C_1$ to $C_4$ alkyl, $C_1$ to $C_4$ haloalkyl, $C_1$ to $C_4$ alkoxy, $C_1$ to $C_4$ alkylthio, $C_1$ to $C_4$ alkylsulfonyl, nitro, phenyl substituted with $R^6$, phenoxy substituted with $R^6$;
$R^6$ is hydrogen, 1 to 2 halogen, methyl, trifluoromethyl, methoxy.

5. The method of claim 4 wherein:
$R^5$ is hydrogen, halogen, methyl, trifluoromethyl, methoxy, phenoxy substituted with hydrogen or 1 to 2 of the following: halogen, methyl, methoxy or trifluoromethyl, nitro;
$R^6$ is hydrogen, halogen, methyl, methoxy, or trifluoromethyl.

6. The method of claim 1 wherein the compound is: 5-methyl-5-phenyl-3-(phenylamino)-2-thioxo-4-oxazolidinone.

7. The method of claim 1 wherein the compound is: 5-(4-fluorophenyl)-5-methyl-3-(phenylamino)-2-thioxo-4-oxazolidinone.

8. The method of claim 1 wherein the compound is: 5-methyl-5-(4-phenoxyphenyl)-3-(phenylamino)-2-thioxo-4-oxazolidinone.

* * * * *